United States Patent [19]

Herlitze

[11] Patent Number: 4,504,268
[45] Date of Patent: Mar. 12, 1985

[54] STIFFENING CORE FOR A CATHETER TUBE

[75] Inventor: Gerhard Herlitze, Baunatal, Fed. Rep. of Germany

[73] Assignee: Intermedicate GmbH, Emmenbrucke, Switzerland

[21] Appl. No.: 438,458

[22] Filed: Nov. 2, 1982

[30] Foreign Application Priority Data

Nov. 10, 1981 [DE] Fed. Rep. of Germany ... 8132839[U]

[51] Int. Cl.³ ............................................. A61M 25/00
[52] U.S. Cl. ...................................... 604/170; 604/280
[58] Field of Search .................. 604/170, 280–284, 604/95; 128/341, 772, 657

[56] References Cited

U.S. PATENT DOCUMENTS

| 2,221,138 | 11/1940 | Hendrickson | 128/341 |
| 3,572,333 | 10/1968 | Hubert | 604/170 |
| 3,612,058 | 10/1971 | Ackerman | 128/772 |
| 4,257,421 | 3/1981 | Beal | 604/170 |
| 4,345,602 | 8/1982 | Yoshimura et al. | 604/280 |
| 4,362,163 | 12/1982 | Krick | 604/280 |

Primary Examiner—Dalton L. Truluck
Attorney, Agent, or Firm—Kenyon & Kenyon

[57] ABSTRACT

A stiffening core of plastic for the gap-free filling of the lumen (i.e., bore) of a catheter tube comprises at least one resilient multifilament strand of high tensile strength which is embedded in a plastic rod. Such a stiffening core contributes to improving the catheter tube's suitability for projection on an x-ray screen.

12 Claims, 3 Drawing Figures

STIFFENING CORE FOR A CATHETER TUBE

The invention relates to a stiffening core of plastic for the gap-free filling of the lumen of a catheter tube, which core inhibits the backflow of blood, facilitates the introduction of the catheter tube into a blood vessel, and improves its projection on an x-ray screen.

Long-term therapy involving infusion solutions is initiated perferably by means of venous catheters. Several forms of venous catheters are known, which differ in their length, diameter, and technique of application. Usually venous catheters are installed without the aid of an x-ray screen, in which case, however, the position of the cathether in the body is subsequently checked.

In some cases, as for instance when installing a catheter leading to the heart, the advance and the position of the catheter tube must be followed on an x-ray screen. In order that the catheter tube may be projected on an x-ray screen, either the catheter tube itself is provided with radiologically visible contrast strips, or is manufactured from a plastic comprising in part a radiologically visible substance (i.e., an x-ray contrast substance) substantially homogenously distributed in the plastic, or a stiffening core, made of a plastic containing an x-ray contrast medium and filling the lumen of the catheter tube, is used for improved projection on an x-ray screen. However, the x-ray contrast substances admixed in the various types of plastics reduce the strength of the plastic and considerably impair their tensile strength, depending on the percentage amount employed. This may lead to breaking the stiffening core, which is dangerous to the patient.

Another disadvantage of known stiffening cores made of plastic is that the desired stiffness and resilience can be varied within only a small range. Because of their physical properties, such stiffening cores are also not suitable for being used as a guide bar for a venous catheter to be positioned in body cavities, as practiced in the so-called Seldinger method. In the Seldinger method, helically wound wires in good working order are employed as a stiffening core for a catheter tube, but because of their complicated construction and being an article suitable for only a single use, they are quite expensive.

An object of the invention is to provide a lumen-filling, stiffening core element for a catheter tube, in such a way that, combined with low-cost manufacture, it is resilient and resistant to breaking, and contributes to improving the catheter tube's suitability for detection by x-rays.

This objective has been achieved by employing at least one resilient multifilament strand of high tensile strength embedded in a plastic rod.

The strand imparts high tensile strength to the plastic rod encasing it, thereby enabling the rod to be made of plastics having a high percentage of an x-ray contrast substance without risk of the stiffening core breaking. In this way, the catheter tube, whose lumen (i.e., the bore of the tube) is filled by the stiffening core, becomes clearly visible on an x-ray screen and its movement and position can be observed reliably. If the strand itself is made of radiologically visible material, it supplements the effect of the x-ray contrast substance in the plastic, or replaces it when plastic without any contrast substance has been employed for the manufacture of the plastic rod. The stiffening core excels by reason of its appropriate stiffness and good resilience. Both factors can be varied widely by appropriate selection of the diameter and of the number of the monofilaments of the strand, and hence can be adjusted to the desired use of the catheter. Due to the plastic rod, a smooth surface results which by the selection of a suitable material, for instance polyethylene, poly-tetrafluoroethylene or polyurethane, counteracts blood coagulation.

As an advantageous development of the invention, the strand is arranged concentrically in the plastic rod.

Each strand may consist of monofilaments of different materials or of a single material. The individual monofilaments of the strand may have the same or different cross-sectional areas. The physical properties of the stiffening core can also be modified by this feature.

The cross-section of the monofilaments may be circular, or may be of other design, e.g., multilobal, or in the shape of a Y, as from some processes of spinning multifilament yarns. The strand may be twisted or braided. It may be made in left-hand or right-hand lay.

Advantageously, the strand consists of monofilaments of a non-rusting material, preferably steel wires.

The plastic rod may consist of a plurality of plastics, or it may be manufactured from a single plastic material.

The stiffening core can be used as a guide bar for a catheter to be introduced into body cavities if a highly flexible tip of plastic is firmly connected to the insertion-end of the plastic rod. The tip may be solid or hollow in the form of a pipe nipple. It should be securely joined to the plastic cladding of the strand. In this design, the stiffening core for a catheter tube constitutes a low-cost guide element suitable for single use for the positioning and position correction of catheters. With this stiffening core of defined stiffness, having a highly flexible tip, obstacles in the course of curved body cavities, in particular in veins, not otherwise passable, can be overcome and incorrect or misguided positions can be corrected, with the potentiality of exact control by means of an x-ray monitor.

An embodiment of the invention is illustrated schematically in the drawings, in which -

Figure 1:
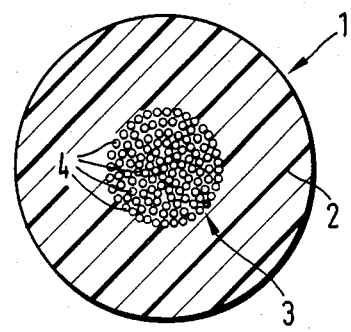
FIG. 1 is a transverse section of the stiffening core.
Figure 2:
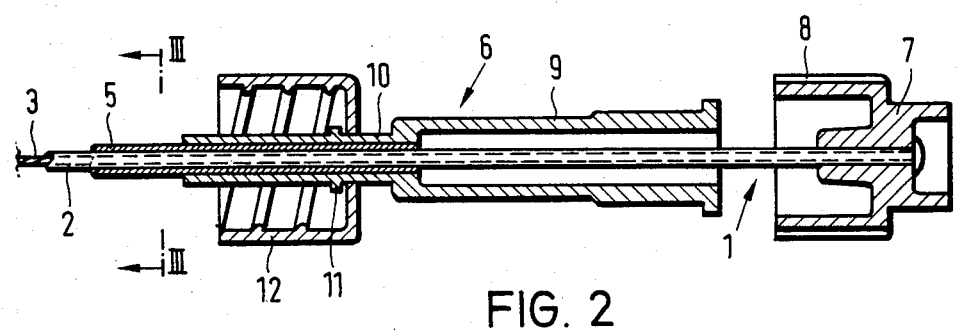
FIG. 2 is a longitudinal section of a catheter with a stiffening core.
Figure 3:
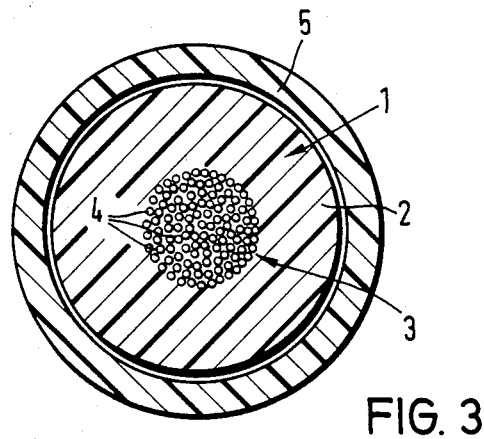
FIG. 3 is a transverse section along line 3—3 of FIG. 2.

The stiffening core 1 for filling, in slideable engagement, the lumen of a catheter tube 5, in particular of a venous catheter 6, consists of a plastic rod 2 of suitable material, for example, polyethylene, poly-tetrafluoroethylene or polyurethane, which counteracts blood coagulation. The plastic may contain an x-ray contrast substance. The stiffening core 1 has a circular cross-section, and in its center is a non-tearing (i.e., high tensile strength) and resilient strand 3 fixedly embedded in the rod 2. The strand 3 comprises a plurality of monofilaments 4. In the embodiment depicted, the diameter of the monofilaments 4 is uniform. The strand 3 consists preferably of steel wires, so that they improve the projection on an x-ray screen of the position of stiffening core 1 and hence of the catheter tube 5 surrounding it. Thus, strand 3 imparts high tensile strength and resilience to the stiffening core 1. This has the advantage of preventing the breaking of the stiffening core, especially when the plastic rod 2 comprises a large fraction of an x-ray contrast substance; and also furnishes stiffening core 1 with good guiding properties during insertion into curved body cavities.

The physical properties (e.g., tensile strength and resilience) of the stiffening core 1 can be varied at will for adaptation to desired purposes of use, by varying the number and/or the diameter of the individual monofilaments 4, as well as the type of plastic used for the plastic rod 2.

At one end of the stiffening core 1, a cap-type gripping piece 7 is attached, the outside of which is provided with a knurl 8. In the embodiment depicted, the gripping piece 7 loosely spans the end of a catheter adapter 9, in whose connecting piece 10, the catheter tube 5 is inserted and fastened. A collar 11 serves to prevent slipping of a nut 12 for coupling the catheter adapter 9 to a connecting part.

If a highly flexible tip is provided at the insertion-side end of the stiffening core 1, the latter can be used not only as a lumen-filling stiffening element for a catheter tube 5, but also as a guide bar for a venous catheter 6 to be positioned in body cavities by the so-called Seldinger method. Because it can be manufactured at low cost, the stiffening core 1 is suitable for single use.

While the apparatus described herein constitute preferred embodiments of the invention, it is to be understood that there are variations in materials and equipment which may be employed which are included in the invention as defined by the appended claims. Therefore, the detailed description should be considered illustrative rather than as restrictive.

Having thus described the invention, what is claimed is:

1. Catheter apparatus comprising a tubular catheter and a stiffening core, said catheter having a lumen, said stiffening core comprising a cylindrical plastic rod, said rod being disposed in said lumen in gap-free relationship therewith and being slidably removable from said lumen, said rod comprising at least one resilient multifilament strand of high tensile strength and uniform diameter fixedly embedded therein.

2. A stiffening core according to claim 1, characterized by having a single strand embedded concentrically in said rod.

3. A stiffening core according to claim 1, characterized in that said strand consists of monofilaments of different materials.

4. A stiffening core according to claim 1, characterized in that said strand consists of monofilaments of a single material.

5. A stiffening core according to claim 4, characterized in that said strand consists of monofilaments of a nonrusting steel.

6. A stiffening core according to claim 1, characterized in that said monofilaments are of equal cross-sectional area.

7. A stiffening core according to claim 1, characterized in that said monofilaments of the strand have mutually varying cross-sectional areas.

8. A stiffening core according to claim 1, characterized in that the lay of the strand is left-hand or right-hand.

9. A stiffening core according to claim 1, characterized in that said rod is comprised of a plurality of plastic materials.

10. A stiffening core according to claim 1, characterized in that a highly flexible tip of plastic is firmly connected to the insertion end of said core.

11. A stiffening core according to claim 10, characterized in that said tip is hollow.

12. A stiffening core according to claim 10, characterized in that the tip is solid.

* * * * *